US00PP09414P

United States Patent [19]

Meilland

[11] Patent Number: Plant 9,414

[45] Date of Patent: Jan. 2, 1996

[54] MINIATURE ROSE PLANT NAMED 'MEIGLOYEL'

[75] Inventor: Alain A. Meilland, Antibes, France

[73] Assignee: The Conard-Pyle Company, West Grove, Pa.

[21] Appl. No.: 384,731

[22] Filed: Feb. 7, 1995

[51] Int. Cl.[6] ..... A01H 5/00

[52] U.S. Cl. ..... Plt./8.2

[58] Field of Search ..... Plt./8.2

[56] References Cited

U.S. PATENT DOCUMENTS

P.P. 4,265 6/1978 Schwartz ..... Plt./8.2

P.P. 6,177 5/1988 Meilland ..... Plt./8.2

P.P. 8,011 10/1992 Olesen et al. ..... Plt./8.2

*Primary Examiner*—Howard J. Locker

*Attorney, Agent, or Firm*—Burns, Doane, Swecker & Mathis

[57] ABSTRACT

A new and distinct variety of rose plant of the miniature class is provided which abundantly forms attractive double Chinese Yellow blossoms which are stable and will retain their coloration upon the passage of time. The plant is bushy and dense with considerable branching. The blossoms possess a light fragrance. The plant is well adapted to pot forcing under greenhouse growing conditions, and grows well on its own roots. Also, the plant can be grown as attractive ornamentation in the landscape.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the product of the pollination of the Meigronuri variety (U.S. Plant Pat. No. 4,625) and the Yellow Pages variety (non-patented in the United States). The male parent (i.e., the pollen parent) of the new variety was the product of the pollination of the Schobitet variety (U.S. Plant Pat. No. 5,690) and the Lavglo variety (U.S. Plant Pat. No. 7,136). The parentage of the new variety can be summarized as follows:

(MEIGRONURI×YELLOW PAGES)×(SCHOBITET×LAVGLO).

The seeds resulting from the above pollination were sown and 18 small plants were obtained which were physically and biologically different from each other. Selective study resulted in the identification of a single plant of the new variety.

It was found that the new variety of miniature rose plant of the present invention possesses the following combination of characteristics:

(a) forms in abundance attractive double blossoms which stably exhibit Chinese Yellow coloration under greenhouse growing conditions, (b) exhibits a bushy growth habit with considerable branching, and (c) possesses a good ability to undergo pot forcing under greenhouse growing conditions.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the Meigloyel variety.

BRIED DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during July while growing on their own roots outdoors at LeCannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates a specimen of a flower during the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets with the upper surface being shown at the bottom and the under surface being shown at the top;

FIG. 15 — illustrates specimens of leaves with five leaflets with the upper surface being shown at the top and the under surface being shown at the bottom; and FIG. 16 — illustrates specimens of leaves with seven leaflets with the upper surface being shown at the right and the under surface being shown at the left.

DETAILED DESCRIPTION

Figures 1, 2, 3, 4, 5, 6, 7, 8, 9, 10, 11, 12, 13, 14, 15, 16:
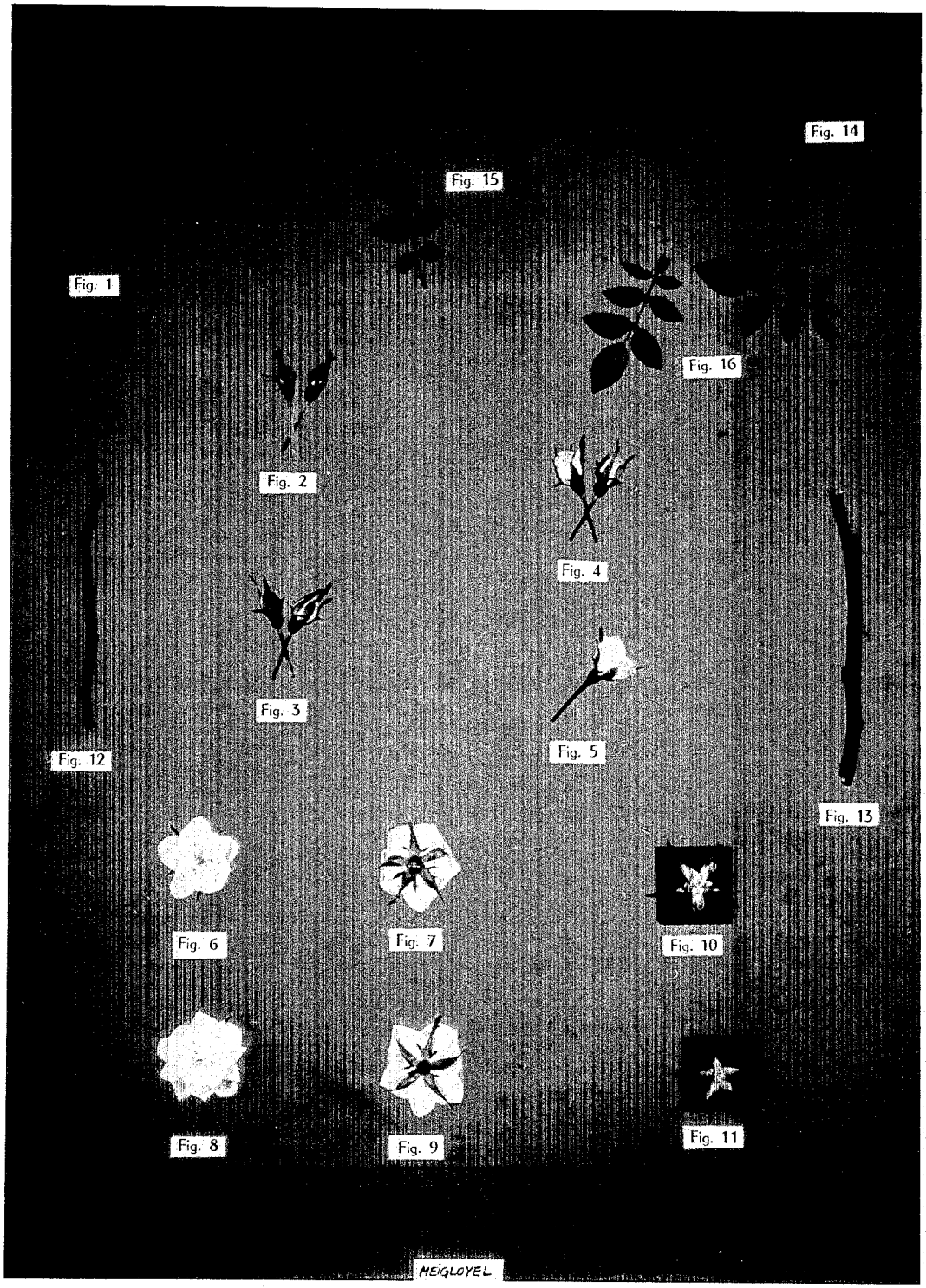

The chart used in the identification of the colors is that of The Royal Horticultural Society (R.H.S. Colour Chart). The terminology which precedes reference to the chart has been added to indicate the corresponding colors in more common terms. The description is based on two year-old specimens of the new variety which were observed during September while growing on their own roots outdoors at LeCannet des Maures, Var, France.

Class: Miniature.

Plant:

*Height.*—Approximately 25 cm. on average at the end of the growing season.

*Habit.*—Bushy.

Branches:

*Color.*—Young stems: light green, Green Group 137C. adult wood: medium green, Green Group 137B.

*Thorns.*—Quantity: none.

Leaves:

*Petioles.*—Upper surface: striped, reddish on young foliage and medium green on mature foliage with less glandular edges. Under surface: light green and rarely bear small prickles.

*Stipules.*—Adnate, pectinate, narrow and linear.

Leaflets.—Number: 3, 5, and 7. Shape: oval. Texture: normal. General appearance: dense and dull foliage. Color (young foliage): Upper surface: medium green, Green Group 137B. Under surface: light green, Green Group 137C. Color (adult foliage): Upper surface: dark green, Green Group 139A. Under surface: medium green, Green Group 137B.

Inflorescence:

*Number of flowers.*—Usually one per stem and sometimes up to approximately three per stem.

*Peduncle.*—Medium green, smooth, and the length is approximately 2 cm. on average.

*Sepals.*—Upper surface: tomentose and greenish in coloration. under surface: medium green with a few extensions.

*Buds.*—Shape: egg-shaped. Length: approximately 1.5 cm. on average. Size: small for this class. Color upon opening: Upper surface: Chinese Yellow, Yellow-Orange Group 16A. Under surface: Chinese Yellow, Yellow-Orange Group 16B.

*Flower.*—Form: cupped at opening. Diameter: approximately 3 cm. on average. Color (when opening begins): Upper surface: Chinese Yellow, Yellow-Orange Group 16A. Under surface: Chinese Yellow, Yellow-Orange Group 16B. Color (when blooming): Upper surface: Chinese Yellow, Yellow-Orange Group 16A. Under surface: Chinese Yellow, Yellow-Orange Group 16B. Color (at end of blooming): Upper surface: Chinese Yellow, Yellow-Orange Group 16A. Under surface: Chinese Yellow, Yellow-Orange Group 16B. Fragrance: light. Lasting quality: medium. Petal number: approximately 26 on average. Petal shape: external petals are rounded with reflexed edges and the inside petals are oval. Petal drop: good. Anthers: normal and ochre in coloration. Stamen number: approximately 32 on average. Filaments: bright yellow. Pistil number: approximately 18 to 25 on average. Stigmas: normal and strawlike in appearance. Styles: greenish in coloration. Receptacle: medium green, smooth, and in longitudinal section in the shape of a pitcher.

Development:

*Vegetation.*—Medium.

*Blooming.*—Abundant.

*Aptitude to bear fruit.*—Poor.

*Resistance to diseases.*—Medium.

I claim:

1. A new and distinct variety of miniature rose plant characterized by the following combination of characteristics:

(a) forms in abundance attractive double blossoms which stably exhibit Chinese Yellow coloration under greenhouse growing conditions, (b) exhibits a bushy growth habit with considerable branching, and (c) possesses a good ability to undergo pot forcing under greenhouse growing conditions;

substantially as herein shown and described.

* * * * *

MEIGLOYEL